US010773039B2

(12) United States Patent
Vicario et al.

(10) Patent No.: US 10,773,039 B2
(45) Date of Patent: Sep. 15, 2020

(54) EXPIRATORY FLOW LIMITATION DETECTION USING PRESSURE PERTURBATIONS

(71) Applicant: KONINKLIJKE PHILIPS N.V., Eindhoven (NL)

(72) Inventors: Francesco Vicario, Boston, MA (US); William Anthony Truschel, Oakmont, PA (US)

(73) Assignee: Koninklijke Philips N.V., Eindhoven (NL)

( * ) Notice: Subject to any disclaimer, the term of this patent is extended or adjusted under 35 U.S.C. 154(b) by 194 days.

(21) Appl. No.: 15/987,062

(22) Filed: May 23, 2018

(65) Prior Publication Data
US 2018/0339120 A1 Nov. 29, 2018

Related U.S. Application Data

(60) Provisional application No. 62/510,388, filed on May 24, 2017.

(51) Int. Cl.
*A61M 16/00* (2006.01)
*A61B 5/085* (2006.01)
(Continued)

(52) U.S. Cl.
CPC .......... *A61M 16/024* (2017.08); *A61B 5/085* (2013.01); *A61B 5/0816* (2013.01);
(Continued)

(58) Field of Classification Search
CPC .............. A61M 13/00; A61M 16/0003; A61M 16/0006; A61M 16/0057;
(Continued)

(56) References Cited

U.S. PATENT DOCUMENTS 5,704,345 A * 1/1998 Berthon-Jones ....... A61B 5/087
128/204.23
6,588,422 B1 * 7/2003 Berthon-Jones ...... A61M 16/00
128/204.23
(Continued)

FOREIGN PATENT DOCUMENTS

WO WO2016079703 A1 5/2016

OTHER PUBLICATIONS

Khirani, S. et al., "Identification of a Non-Linear Model as a New Method to Detect Expiratory Airflow Limitation in Mechanically Ventilated Patients", Acta Biotheoretica, Dec. 2004, vol. 52, Issue 4, pp. 241-254.
(Continued)

*Primary Examiner* — Rachel T. Sippel
*Assistant Examiner* — Benjamin M. Kusiak
(74) *Attorney, Agent, or Firm* — Daniel H. Brean

(57) ABSTRACT

A system and a method for expiratory flow limitation (EFL) detection by controlling positive pressure (e.g., PEEP) applied during expiration for a subject is based on a temporary perturbation or adjustment of a pressure level of positive pressure during exhalation on selected breaths. The different responses to such a perturbation of flow-limited breaths compared to non-flow limited breaths is used to assess EFL in a subject. Automatic adjustments of the positive pressure applied to the patient are used in the disclosed algorithm to abolish EFL, and are implemented through existing ventilators and other respiratory devices.

23 Claims, 6 Drawing Sheets

(51) Int. Cl.
  *A61B 5/08* (2006.01)
  *A61B 5/087* (2006.01)
  *A61M 16/20* (2006.01)
  *A61B 5/091* (2006.01)

(52) U.S. Cl.
  CPC ....... *A61B 5/0871* (2013.01); *A61M 16/0003* (2014.02); *A61M 16/0057* (2013.01); *A61M 16/026* (2017.08); *A61B 5/091* (2013.01); *A61M 16/0069* (2014.02); *A61M 16/202* (2014.02); *A61M 16/205* (2014.02); *A61M 2016/0027* (2013.01); *A61M 2016/0033* (2013.01); *A61M 2016/0042* (2013.01); *A61M 2205/3331* (2013.01); *A61M 2205/3365* (2013.01); *A61M 2205/3368* (2013.01); *A61M 2205/3375* (2013.01); *A61M 2205/50* (2013.01)

(58) Field of Classification Search
  CPC ... A61M 16/021–026; A61M 2016/003–0042; A61M 2205/07; A61M 2205/33; A61M 2205/3303; A61M 2205/3327; A61M 2205/3331; A61M 2205/3334; A61M 2205/35; A61M 2205/3546–3592; A61M 2205/50–505; A61M 2205/70–702; A61M 16/005; A61B 5/087; A61B 5/0871; A61B 5/091
  USPC ............ 128/204.23, 204.18, 204.21, 204.26
  See application file for complete search history.

(56) References Cited

U.S. PATENT DOCUMENTS

| 10,064,583 | B2* | 9/2018 | Nakai | A61M 16/026 |
|---|---|---|---|---|
| 10,105,506 | B2* | 10/2018 | Bassin | A61M 16/024 |
| 10,335,566 | B2* | 7/2019 | Kulstad | A61M 16/024 |
| 2005/0178385 | A1* | 8/2005 | Dellaca' | A61B 5/085 |
| | | | | 128/204.23 |
| 2008/0092894 | A1* | 4/2008 | Nicolazzi | A61M 16/0051 |
| | | | | 128/204.23 |
| 2008/0295839 | A1* | 12/2008 | Habashi | A61M 16/0069 |
| | | | | 128/204.22 |
| 2010/0147305 | A1 | 6/2010 | Dellaca' | |
| 2010/0275921 | A1* | 11/2010 | Schindhelm | G16H 20/40 |
| | | | | 128/204.23 |
| 2014/0290658 | A1* | 10/2014 | Schindhelm | A61B 5/0205 |
| | | | | 128/204.23 |
| 2015/0320955 | A1 | 11/2015 | Mahadevan | |
| 2016/0022938 | A1 | 1/2016 | Rapoport et al. | |

OTHER PUBLICATIONS

Armaganidis et al: "Instrinsic Positive End-Expiratory Pressure in Mechanically Ventilated Patients With and Without Tidal Expiratyory Flow Limitation"; Crit Care Med 2000, vol. 28, No. 12, pp. 3837-3842.

Dellaca, R.L. et al., "Noninvasive detection of expiratory flow limitaiton in COPD patients during nasal CPAP". European Respiratory Journal, vol. 27, No. 5 (May 1, 2006), pp. 983-991.

\* cited by examiner

EXPIRATORY FLOW LIMITATION DETECTION USING PRESSURE PERTURBATIONS

CROSS-REFERENCE TO RELATED APPLICATIONS

This patent application claims the priority benefit under 35 U.S.C. § 119(e) of U.S. Provisional Application No. 62/510,388 filed on May 24, 2017, the contents of which are herein incorporated by reference.

BACKGROUND

1. Field

The present disclosure pertains to a method and a system for detecting expiratory flow limitation (EFL) by controlling pressure to a subject's airway.

2. Description of the Related Art

Chronic obstructive pulmonary disease (COPD) is a major public health problem. It is the fourth leading cause of chronic morbidity and mortality in the United States, affecting over 24 million Americans. It is the third leading cause of death in the United States after heart disease and cancer, and by the 2020s it is projected to be the third leading cause of death worldwide. The increased mortality is driven by the expanding epidemic of smoking and the aging population worldwide.

COPD is an umbrella term used to describe progressive lung diseases including emphysema, chronic bronchitis, non-reversible asthma, and some forms of bronchiectasis. COPD is characterized by increasing breathlessness. Patients with COPD may have difficulty exhaling because of the deterioration of their lung tissue or the inflammation of their airway walls. This condition is commonly referred to as Expiratory Flow Limitation (EFL). EFL seriously affects the quality of life and can ultimately contribute to acute respiratory failure.

Common treatments for EFL are Positive end expiratory pressure, PEEP, and/or pharmaceuticals. The level of PEEP to be applied to a patient is generally determined in a more or less arbitrary fashion.

With patients in the ICU, EFL is typically detected with a manual maneuver that is externally applied to the patient's body. For example, a clinician or respiratory therapist typically exerts force on the patient's abdomen at the onset of exhalation. This force causes an increase in the pressure difference between the lungs and mouth that should drive the exhalation flow. If the patient has EFL, the exhalation flow does not increase. This technique, however, is not applicable for a chronic patient at home.

Other techniques for the detection of EFL are the ΔXrs with forced oscillation technique (FOT) and the negative expiratory pressure (NEP) method. Such methods are available as stand-alone devices or as part of multifunctional spirometers. These techniques are typically used for non-ventilated patients. The NEP method is conceptually similar to the application of pressure on the abdomen. It replaces the increasing pressure in the lungs from abdominal compression with negative pressure applied at the mouth. The ΔXrs with FOT method relies on the change in the reactance of the respiratory system when EFL occurs. In order to "measure" the reactance, a forced sinusoidal pressure signal is applied.

SUMMARY

Accordingly, one or more aspects of the present disclosure relate to a system for determining expiratory flow limitation (EFL) by controlling positive pressure applied during expiration of a breath in a subject (e.g., that is undergoing pressure (e.g., Bi-level) treatment with mechanical ventilation). The disclosed system includes: a pressure generator configured to generate a positive pressurized flow of breathable gas for delivery to an airway of the subject; one or more sensors configured to generate output signals conveying information related to breathing of the subject; and one or more hardware processors operatively coupled to the pressure generator and the one or more sensors. The one or more processors are configured by machine-readable instructions to: cause the pressure generator to deliver the positive pressurized flow of breathable gas at a set pressure level to the subject for a series of breaths; for at least one selected breath in the series of breaths, cause the pressure generator to temporarily alter the pressure level of the positive pressurized flow of breathable gas to a pressure that is different from the set pressure level for delivery to the subject during exhalation of the at least one selected breath; determine EFL in the subject using the output signals from the one or more sensors conveying information related to (a) exhalation for the series of breaths of the subject at the set pressure level and (b) exhalation for the at least one selected breath at the altered pressure level; and automatically adjust, without user intervention, the set pressure level of the pressure generator based on the EFL determination for delivery of the positive pressurized flow of breathable gas to the subject at an adjusted pressure level for at least one subsequent breath.

Another aspect of the present disclosure relates to a method for determining EFL by controlling positive pressure applied during expiration of a breath to a subject's airway with a system, wherein the system includes a pressure generator, one or more sensors, and one or more hardware processors. The method includes: generating, with the pressure generator, a positive pressurized flow of breathable gas during the patient's expiration at a set pressure level and at an altered pressure level that has a different pressure from that of the set pressure level for delivery to an airway of the subject; generating, with the one or more sensors, output signals conveying sensed information related to (a) exhalation for a series of breaths of the subject at the set pressure level and (b) exhalation for at least one selected breath at the altered pressure level; determining, using the one or more hardware processors, a percentage of exhaled volume of air for (a) at least one reference breath from the series of breaths and (b) the at least one selected breath based on the generated output signals of the sensed information; comparing, using the one or more hardware processors, the determined percentage of exhaled volume of air for both the at least one reference breath and the at least one selected breath; determining, using the one or more hardware processors, EFL in the subject based on the comparison; and causing, using the one or more hardware processors, automatic adjustment, without user intervention, of the set pressure level of the pressure generator based on the EFL determination for delivery of the positive pressurized flow of breathable gas to the subject at an adjusted pressure level for at least one subsequent breath.

Still another aspect of the present disclosure relates to a system for determining EFL by controlling positive pressure applied during expiration of a breath in a subject undergoing treatment with mechanical ventilation. The system includes: means for generating a positive pressurized flow of breathable gas at a set pressure level and at an altered pressure level that has a different pressure from that of the set pressure level for delivery to an airway of the subject; means for generating output signals conveying sensed information related to (a) exhalation for a series of breaths of the subject at the set pressure level and (b) exhalation for at least one selected breath at the altered pressure level; means for determining EFL in the subject by comparing data from the output signals of at least one reference breath from the series of breaths and the at least one selected breath against a threshold; and means for automatically adjusting, without user intervention, the set pressure level of the means based on the EFL determination for delivery of the positive pressurized flow of breathable gas to the subject at an adjusted pressure level for at least one subsequent breath.

These and other features and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
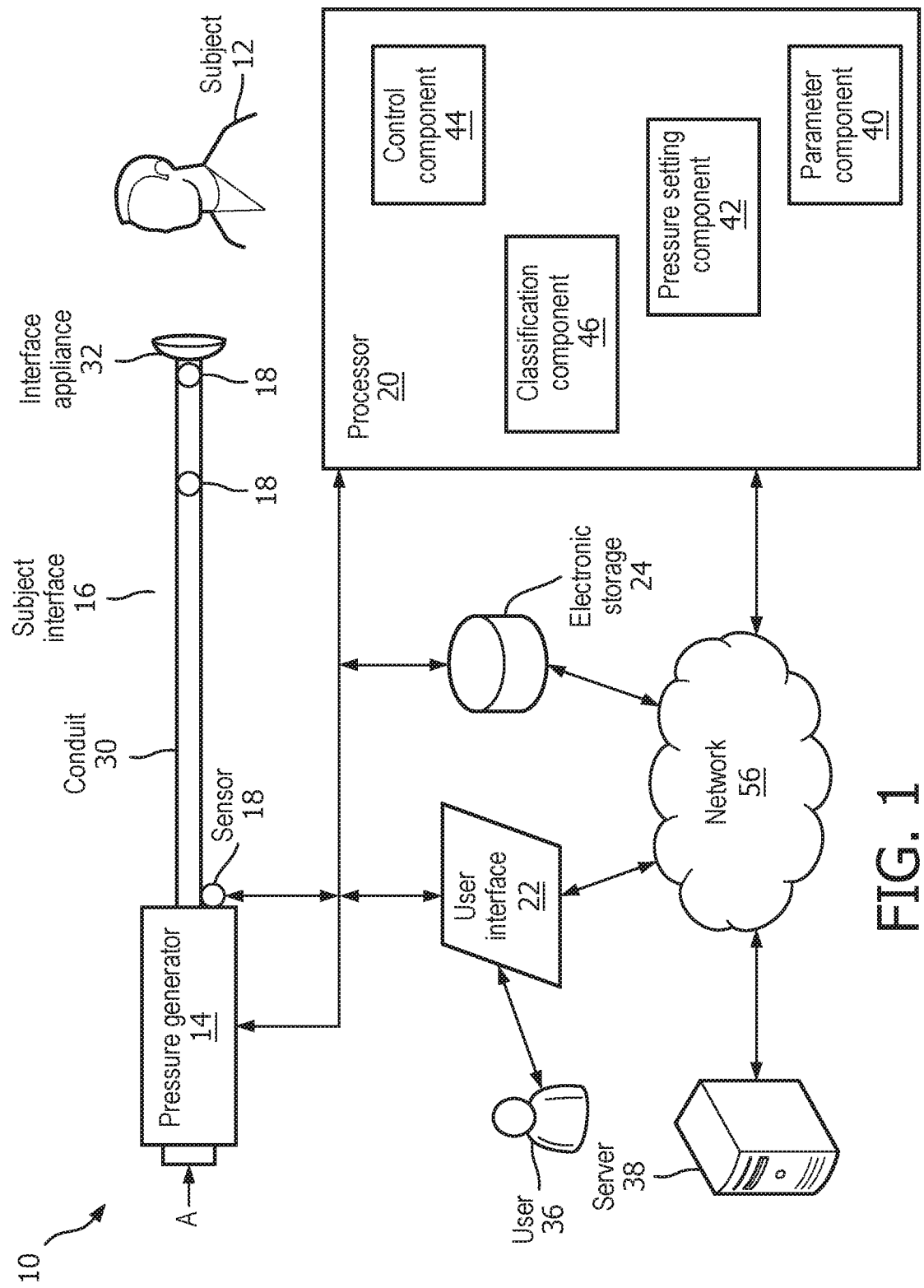
FIG. 1 is a schematic illustration of a system configured to detect expiratory flow limitation (EFL) by controlling positive pressure delivered to a subject in accordance with an embodiment of this disclosure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Also, the terms "subject" and "patient" are used interchangeably throughout this disclosure to refer to a user of the herein disclosed system 10 that receives a pressurized flow of breathable gas to his/her airway.

As noted above, COPD refers to describe progressive lung diseases including emphysema, chronic bronchitis, non-reversible asthma, and some forms of bronchiectasis. Expiratory Flow Limitation (EFL) refers to a condition wherein a subject or patient has difficulty exhaling because of breathlessness due to deterioration of their lung tissue or inflammation of their airway walls, or even airflow obstruction. Patients with COPD or similar lung diseases are commonly diagnosed with EFL. Typically, EFL requires the subject to breathe at higher lung volumes to produce a necessary expiratory flow.

As used herein, a breath taken by a subject or patient refers to inhaling and exhaling; that is, each breath comprises an inhalation part (I) and an exhalation part (E). The invention proposes an EFL detection technique that is based on a temporary perturbation of pressure during exhalation on selected breaths and that detects EFL based on the different response to such a perturbation that flow-limited breaths have compared to non-flow limited breaths.

More specifically, this disclosure provides three main elements: a temporary change in pressure level of positive pressurized flow during exhalation on one or more selected breaths to probe the respiratory system specifically for EFL detection, a determination or classification algorithm to process the exhalation flow (waveform) of the breath with changed pressure level against that of an undisturbed or reference breath (or breaths) (at a set pressure level) to determine EFL, and an adjustment (increase or decrease) of the set pressure level based on the determination of EFL. The first element is meant to increase the exhalation driving pressure similarly to the traditional manual maneuver of force on the abdomen described above. The second element, or classification algorithm, determines if the patient is exhalation flow limited at the set pressure level. The third element adjusts pressure accordingly to treat EFL.

As described in greater detail below, the disclosed system and method may be used as a diagnostic tool, where the patient is temporarily placed on the EFL detection device, that includes at least a pressure device (or pressure generator) and microprocessor, or a short period of time, during which the device is used to determine if the patient has EFL.

In accordance with an embodiment, the disclosed EFL detection technique/system is used with a ventilating device, such as a bi-level positive airway pressure support (BiPAP), and an EFL determination is made based on a temporary perturbation of PEEP during exhalation on selected breaths, and the different response to such a perturbation that flow-limited breaths have compared to non-flow limited breaths. Positive end-expiratory pressure (PEEP) is the pressure in the lungs (e.g., alveolar pressure) above atmospheric pressure (the pressure outside of the body) that exists at the end of expiration and includes applying a constant positive pressure to the patient's airways during expiration (while avoiding expiratory lung collapse). For example, a temporary change in PEEP level of pressurized flow during exhalation on one or more selected breaths may be used to probe the respiratory system specifically for EFL detection, then a determination or classification algorithm may be used to process the exhalation flow (waveform) of the breath with changed PEEP level against that of an undisturbed or reference breath (or breaths) to determine EFL, and an adjustment (increase or decrease) of the set PEEP may be made based on the determination of EFL.

As a non-limiting example, FIG. 1 is a schematic illustration of a system 10 for determining expiratory flow limitation (EFL) in a subject 12 by controlling positive end expiratory pressure (PEEP) in the subject 12. System 10 may be a bi-level positive airway pressure support (BiPAP), or similar mechanical ventilation device, for providing bi-level therapy. In accordance with another embodiment, for example, the system 10 is a continuous positive airway pressure support (variable CPAP), or proportional positive airway pressure support (PPAP), and/or other types of pressure support therapy for ventilating patients using a pressure generating device. Alternatively, in another embodiment, the system 10 may not include a specific machine-related or pressure generating device; for example, the system may comprise a PEP (positive expiratory pressure) valve, wherein the patient is designed to exhale into the device and the PEP device create pressure in the lungs. The methods for altering pressure may include: PEEP perturbation during Bi-level mechanical ventilation, CPAP perturbation during CPAP therapy, and PEP perturbation during a doctor visit with spontaneous tidal breathing (as a diagnostic tool), for example.

Referring back to the illustrative embodiment of FIG. 1, in a mechanical ventilation system like system 10, the positive pressure applied during expiratory phase may be adjusted for EFL detection as disclosed herein. In the case of a bi-level positive pressure device, for example, the pressure support, EPAP or PEEP level may be controlled. For explanatory purposes only, in this disclosure, much of the description and Figures use PEEP level as an example of the pressure level that is controlled with regards to positive pressure that is applied to a subject. However, this disclosure is not intended to be limited to adjusting PEEP levels, but instead pressure levels of positive pressure applied or supped to a subject/patient.

In accordance with an embodiment, controlling pressure/PEEP level includes temporarily altering a PEEP level of pressurized flow for at least one breath when the subject 12 takes a series of breaths at a different set PEEP level. System 10 is configured to dynamically and automatically select and change a PEEP level for delivery to a subject 12 when a subject is determined to have EFL.

As further described below, system 10 is configured to cause delivery of temporary perturbation or adjustment of PEEP/positive pressure that is applied during exhalation (or expiratory phase) on selected breaths within a series of breaths. Since flow-limited breaths have a different response as compared to non-flow limited breaths, their difference may be evaluated (e.g., to each other and/or to a threshold) to assess EFL in the subject. The system 10 is also configured to provide adjustments of PEEP/positive pressure to abolish EFL in the subject.

In some embodiments, system 10 comprises one or more of a pressure generator 14, a subject interface 16, one or more sensors 18, one or more processors 20, a user interface 22, electronic storage(s) 24, and/or other components. System 10 is configured to offers automatic EFL detection and adjustment of PEEP.

Pressure generator 14 may be configured to generate a pressurized flow of breathable gas for delivery to the airway of subject 12 through subject interface 16. Pressure generator 14 may control one or more ventilation parameters of the flow of gas (e.g., rates, pressures, volumes, temperatures, compositions, etc.) for therapeutic purposes, and/or for other purposes. Pressure generator 14 is configured to control one or more ventilation parameters of the pressurized flow of breathable gas according to a prescribed mechanical ventilation therapy regime and/or other therapy regimes, in accordance with an embodiment herein. By way of a non-limiting example, pressure generator 14 may be configured to control a breath rate, a flow rate, a mouth pressure waveform, a positive end expiratory pressure (PEEP), a tidal volume, a minute volume, an inspiratory to expiratory breath phase ratio (e.g., an I:E ratio), and/or other ventilation parameters of the flow of gas.

Pressure generator 14 receives a flow of gas from a gas source, such as the ambient atmosphere (indicated by an arrow A in FIG. 1), and elevates and/or reduces the pressure of that gas for delivery to the airway of subject 12. Pressure generator 14 may take the form of any device that is and/or includes a device capable of delivering gas flow at a pressure to the airway of subject 12, such as, for example, a pump, blower, piston, or bellows, that is capable of elevating and/or reducing the pressure of the received gas for delivery to a patient. Pressure generator 14 may comprise servo controlled valves and/or motors, one or more other valves and/or motors for controlling the pressure and/or flow of gas, and/or other components. This disclosure also contemplates controlling the operating speed of the blower, either alone or in combination with such valves, to control the pressure and/or flow of gas provided to subject 12.

In yet another embodiment in accordance with this disclosure, pressure generator 14 is not a flow gas source for generating pressurized flow that is delivered to a subject (patient), but instead a device for controlling an amount of pressure by which a patient must exhale and/or breathe to produce positive expiratory flow. For example, it may refer to an adjustment mechanism on a valve device such as a screw on a PEP valve.

Subject interface 16 is configured to deliver the pressurized flow of breathable gas to the airway of subject 12 and provide fluid communication between pressure generator 14 and the airway of subject 12. As such, subject interface 16 comprises conduit 30, interface appliance 32, and/or other components. Conduit 30 is configured to convey the pressurized flow of gas to interface appliance 32. Conduit 30 may be a flexible length of hose, or other conduit that places interface appliance 32 in fluid communication with pressure generator 14. Interface appliance 32 is configured to deliver the flow of gas to the airway of subject 12. In some embodiments, interface appliance 32 is non-invasive. As such, interface appliance 32 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full face mask, a total face mask, or other interface appliances that communicate a flow of gas with an airway of a subject.

The present disclosure is not limited to these examples, however. Delivery of the flow of gas to the subject may be performed using any interface appliance, including, in accordance with some embodiments, an invasive interface appliance such as an endotracheal tube and/or other appliances. Accordingly, interface appliance 32 may be invasively engaged with subject 12. Examples of invasive interface appliance 32 may include endotracheal tubes, tracheostomy tubes, and/or other devices.

Subject interface 16 illustrated in FIG. 1 is illustrated generally as a single-limbed interface for the delivery of the pressurized flow of gas to the airway of subject 12, however, this disclosure is not intended to be limiting. For example, a multi-limbed configuration may be utilized. Such a multi-limbed configuration may comprise one inhale limb configured to provide the pressurized flow of gas to the airway of the subject, one exhale limb configured to exhaust gas from the subject, and one leak limb configured to exhaust excess gas from the subject, as well as one or more connectors for connecting limbs with subject interface 16 (e.g., a suction port, one or more valves, etc.). The description of the configurations of subject interface 16 is for illustrative purposes only, and is not intended to be limiting.

One or more sensors 18 are configured to generate output signals conveying information related to breathing of subject 12 and/or other gas and/or breathing parameters. In some embodiments, the information related to breathing of subject 12 includes the flow rate (and/or information related to the flow rate) of the pressurized flow of breathable gas, pressure of the pressurized flow of breathable gas at the mouth of subject 12 and/or other locations, and/or other information. In some embodiments, the information related to breathing of subject 12 may comprise information related to volumes (e.g., tidal volume, minute volume, etc.), pressures (e.g., inhalation pressure, exhalation pressure, etc.), compositions (e.g., concentration(s)) of one or more constituent gasses, a gas temperature, a gas humidity, acceleration, velocity, acoustics, changes in a parameter indicative of respiratory effort by subject 12, and/or other parameters. In some embodiments, sensors 18 may generate output signals substantially continuously, at predetermined intervals, responsive to occurrence of a predetermined event, and/or at other times. In some embodiments, the predetermined intervals, events, and/or other information may be determined at manufacture, based on user input via user interface 22, and/or based on other information.

Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. For example, one or more of sensors 18 may generate an output based on an operating parameter of pressure generator 14 (e.g., a valve driver or motor current, voltage, rotational velocity, and/or other operating parameters).

Although sensors 18 are illustrated at a different locations along and/or within (or in communication with) conduit 30 between interface appliance 32 and pressure generator 14, this is not intended to be limiting. A sensor may be provided at a single location within subject interface 16. Sensors 18 may include sensors disposed in a number of locations, such as for example, within or adjacent pressure generator 14, within (or in communication with) interface appliance 32, in communication with subject 12, within conduit 30, and/or in other locations. For example, sensors 18 may include a flow rate sensor, a pressure sensor conveying information related a pressure of breathable gas at the mouth of subject 12 and/or other locations, a volume sensor, a temperature sensor, an acoustic sensor, a gas composition (e.g., an SpO2 sensor) sensor, and/or other sensors located at various locations in system 10.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

As shown in FIG. 1, processor 20 is configured to execute one or more computer program components. The one or more computer program components may comprise one or more modules including a parameter component 40, a pressure setting component 42, a control component 44, a classification component 46 (e.g., for determining EFL) 46, and/or other components. Processor 20 may be configured to execute components 40, 42, 44, and/or 46 by software; hardware; firmware; some combination of software, hardware, and/or firmware; and/or other mechanisms for configuring processing capabilities on processor 20. In some embodiments, processor 20 may execute one or more of the operations described below, including those in method 600, and/or other operations substantially continuously (e.g., in real-time and/or near real-time), at predetermined intervals, responsive to occurrence of a predetermined event, and/or at other times.

In some embodiments, the predetermined intervals, events, and/or other information may be determined at manufacture, based on user input via user interface 22, and/or based on other information. Each of the one or more computer programmed components comprises a set of algorithms implemented on processor 20 that instructs processor 20 to perform one or more functions related to ventilation therapy, gas delivery malfunction detection, and/or other operations. For example, control component 44 comprises algorithms implemented on processor 20 that instruct processor 20 to perform controlling of pressure generator 14 to generate the pressurized flow of gas. Control component 44 comprises algorithms implemented on processor 20 that instruct processor 20 to provide one or more parameters related to a therapeutic pressure waveform as well as the non-therapeutic pressure waveform to control component 44 such that pressure generator 14 can generate a pressurized flow of gas in accordance with the one or more parameters.

It should be appreciated that although components 40, 42, 44, and 46 are illustrated in FIG. 1 as being co-located within a single processing unit, in implementations in which processor 20 comprises multiple processing units, one or more of components 40, 42, and/or 44 may be located remotely from the other components. The description of the functionality provided by the different components 40, 42, 44, and/or 46 described below is for illustrative purposes, and is not intended to be limiting, as any of components 40, 42, 44, and/or 46 may provide more or less functionality than is described. For example, one or more of components 40, 42, 44, and/or 46 may be eliminated, and some or all of its functionality may be provided by other components 40,

42, 44, and/or 46. As another example, processor 20 may be configured to execute one or more additional components that may perform some or all of the functionality attributed below to one of components 40, 42, 44, and/or 46.

Parameter component 40 is configured to determine and/or provide one or more parameters related to a therapeutic pressure waveform as well as the non-therapeutic pressure waveform to control component 44 such that control component 44 instructs pressure generator 14 to generate a pressurized flow of gas in accordance with the instruction. Parameter component 40 may store an initial set of parameters from manufacturing, an adjusted set of parameters in accordance with user inputs, one or more parameters related to the test analysis, other parameters related to the alarm signal settings, and/or any other parameters related to other components of system 10. In some embodiments, parameter component 44 is configured to provide one or more reference, e.g., a reference flow rate, indicating a baseline flow rate of the responsive flow of gas under a condition that there is no gas delivery malfunction, a reference amplitude indicating an amplitude of a responsive pulse in the response flow of gas under a condition that there is no gas delivery malfunction, etc.

In some embodiments, the one or more reference values may use historical data related to past tests, and can optionally be adjusted or periodically updated by user 36 (e.g., clinicians or physicians) in accordance with new test requirements, such as PEEP, Bi-Level PAP, CPAP, and PPAP therapies. It should be appreciated that the one or more reference values may include other characteristic parameters associated with the responsive flow of gas such as volume, temperature, gas composition, velocity, acceleration, and/or other parameters, and are not limited to the examples set forth above.

Parameter component 40 is configured to determine tidal volume, lung volume, transpulmonary pressure, PEEP, and/or other parameters related to the pressurized flow of breathable gas and/or the breathing of subject 12. In some embodiments, the tidal volume, lung volume, the transpulmonary pressure, PEEP, and/or other parameters are determined based on the information in the output signals (e.g., from sensors 18), determinations of one or more other parameters, and/or other information. For example, lung volume may be determined based on tidal volume by stitching together several measurements of tidal volume. In some embodiments, the information related to the breathing of subject 12 (e.g., the information in the output signals) includes a flow rate of the pressurized flow of breathable gas (Q), a pressure of breathable gas at a mouth of the subject ($P_{ao}$), and/or other information. In some embodiments, determining the tidal volume for subject 12 based on the information in the output signals comprises multiplying the flow rate by a period of time that corresponds to a given breath. In some embodiments, determining the transpulmonary pressure of subject 12 based on the information in the output signals comprises determining an airway resistance (R) and elasticity (E) based on Q and $P_{ao}$, determining alveolar pressure ($P_{al}$) and muscular pressure ($P_{mus}$) in subject 12 based on R and E, and determining the transpulmonary pressure based on $P_{al}$ and $P_{mus}$. Generally, such determinations and parameters are known in the art and thus not discussed in further detail herein.

Pressure Setting component 42 is configured to determine and optionally set a pressure level (e.g., PEEP level) for breathable gas being delivered to subject 12. The pressure level for starting ventilation may be determined based on a patient's history, information in the output signals from sensors 18, the parameters determined by parameter component 44 (e.g., including the lung volume, the transpulmonary pressure, and/or other parameters), predetermined/factory settings, another user (e.g., doctor or clinician), and/or other information. In some embodiments, pressure setting component 42 is configured to set a PEEP level by controlling pressure generator 14 to generate the pressurized flow of breathable gas to subject 12 over a series of breaths by subject 12. Alternatively, in other embodiments, pressure setting component 42 may determine the set pressure/PEEP level while control component 44 implements the setting of the pressure generator at that set pressure/PEEP level, as described later below. Still in yet another embodiment, parameter component 40 may be used to set the pressure/PEEP level, with control component 44 implementing the setting of pressure generator 14. Further, for part of at least one selected breath, the pressure/PEEP level of the positive pressurized flow of breathable gas may be perturbed, i.e., altered, via pressure setting component 42 and/or control component 44.

In one embodiment, the pressure/PEEP level is perturbed or changed during exhalation by the subject 12. Producing a temporary perturbation of pressure/PEEP (e.g., altering the PEEP level of positive pressurized flow) during exhalation on selected breaths allows for collection of data (e.g., via sensors 18) at different pressure levels. As described herein, the data/responses during the set pressure/PEEP level and the perturbed or altered pressure/PEEP level is analyzed to determine if the subject 12 has flow-limited breaths or non-flow limited breaths. The method may include deriving a signal indicative of lung volume, indicative of output, indicative of flow, indicative of pressure, etc. from a plurality of respiratory signals received from the subject 12 as detected by one or more sensors 18, for determining EFL presence. In some embodiments, pressure setting component 42 is configured to determine and/or set pressure level of the pressure generator so that gas is delivered to subject 12 for a series of breaths, followed by delivery of gas to the subject 12 at an altered pressure level—e.g., a reduced positive pressure—for part (exhalation) of at least one breath by altering the pressure level of the pressure generator. Pressure setting component 42 may also then determine and/or reset the pressure generator at the previously set pressure/PEEP level for at least one breath thereafter. Again, the control component 44 may alternately reset the pressure generator at the set pressure/PEEP level that is determined by the pressure setting component 42.

Figure 2:
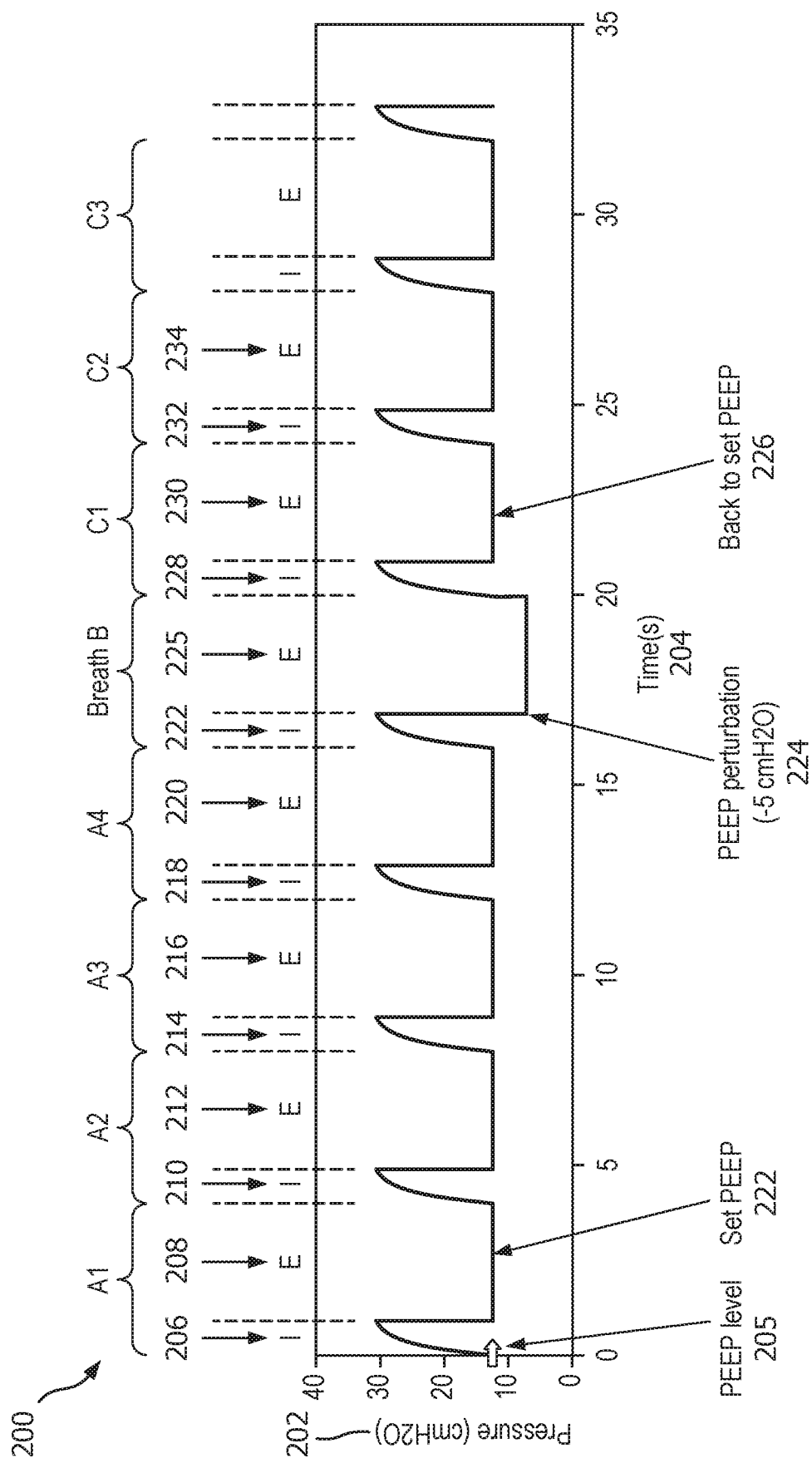
FIG. 2 illustrates an exemplary waveform of pressure v. time for a series of breaths by a subject at a set PEEP level and at least one breath at an altered PEEP level.

FIG. 2 illustrates an exemplary waveform 200 of pressure 202 (measured in cmH2O) vs. time 204 (measured in seconds) for a series of breaths taken by a subject 12 and in accordance with an embodiment. Each breath in the exemplary waveform 200 includes a representation of an inhalation part (I) that typically lasts a couple to few seconds, e.g., 1-2 seconds (shown as 206, 210, 214, 218, 222, 228, 232 in FIG. 2) and an exhalation part (E) that lasts a similar (or longer) amount of time, e.g., 1-4 seconds (shown as 208, 212, 216, 220, 225, 230, 234 in FIG. 2). In this illustrated case, a PEEP level of gas delivered to subject 12 is reduced during exhalation of a selected breath (i.e., a perturbation is introduced to the subject). For example, during one or more breaths, e.g., breath A1 (206+208), breath A2 (210+212), breath A3 (214+216) and breath A4 (218+220) as illustrated in FIG. 2, pressurized air is delivered at a set PEEP level 205, e.g., 12 cmH2O, to the subject's mouth, shown as part 222 of the waveform. For breath B, the PEEP level 205 remains the same for inhalation 222, but at exhalation 225, the PEEP level of the gas delivered to the subject's mouth is altered, e.g., reduced to 7 cmH2O (producing a perturbation of 5 cmH2O or drop in pressure), temporarily for a period of time (e.g., around/approximately four seconds), during the exhalation part E of breath B. The output waveform during PEEP perturbation (e.g., approximately 16-20 seconds) is shown as part 224. At breath C1 (228+230), e.g., during inhalation 228, the PEEP level is set back to the previous PEEP level, e.g., 12 cmH2O, as represented by part 226 of the waveform. The PEEP level 205 may stay the same for one or more exhalations or breaths, e.g., breath C2 (232+234), breath C3, etc., thereafter.

In accordance with embodiments, the amount of perturbation or altering of the set PEEP level for the selected breath(s) may be a preset or standard value, such as 5 cmH2O. However, it is envisioned that an amount of perturbation or altering of the set PEEP level for the selected breath(s) such that an EFL determination may be computed may be determined any number of ways, including, for example, providing an altered PEEP level for the perturbation that is determined based on a predetermined percentage or amount of the set PEEP level. The example alteration noted above is not intended to be limiting.

Additionally, in some embodiments, pressure setting component 42 is configured to determine and set an adjusted PEEP level by controlling pressure generator 14 to generate the pressurized flow of breathable gas to subject 12 over a series of breaths by subject 12, after EFL detection (which is described in greater detail below). For example, the disclosed system 10 is designed such that it is configured to (via processor 20) automatically adjust, without user intervention, the set PEEP level of the pressure generator based on the EFL determination for delivery of the pressurized flow of breathable gas to the subject at an adjusted PEEP level (e.g., for another series of breaths). In some cases, if EFL is detected, the adjusted PEEP level is an increased PEEP level as compared to the set PEEP level. If EFL is not detected, the adjusted PEEP level is a decreased PEEP level as compared to the set PEEP level or the same as set PEEP level. Pressure setting component 42 may be configured to determine and/or set this adjusted PEEP level of the pressure generator 14. Alternatively, pressure setting component 42 may determine an adjustment in the PEEP level while control component 44 implements the setting of the pressure generator 14 at that adjusted PEEP level.

In accordance with embodiments, the adjustment in PEEP level may be a preset or fixed value, such as 0.5 cmH2O or 1 cmH2O. However, it is envisioned that an adjustment in PEEP level may be determined in any number of ways, including, for example, being based on the output signals from sensor 18, including features such as exhaled volume of air, lung volume, transpulmonary pressure, and/or other information as measured or sensed for individual breaths in a series of breaths, or based on a predetermined percentage or amount of the set PEEP level. The example adjustment noted above is not intended to be limiting.

In accordance with some embodiments, the altered and/or adjusted PEEP level may be subject-specific and based on current or previously gathered data from other treatment courses.

Figure 5:
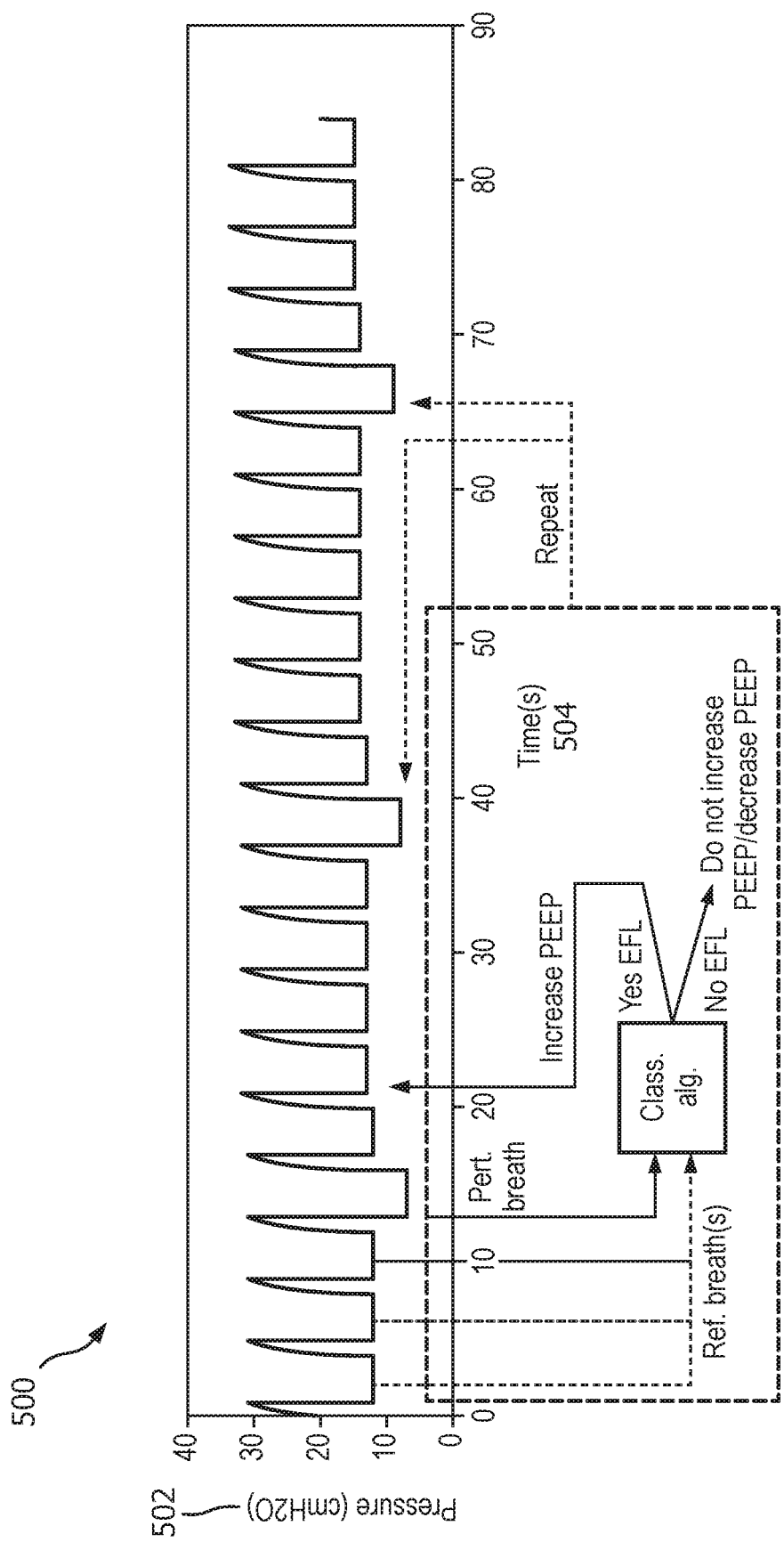
FIG. 5 illustrates an exemplary waveform of pressure v. time for determining EFL and adjusting PEEP levels based on an output determination for different series of breaths by a subject in accordance with an embodiment of this disclosure.

In some embodiments, pressure setting component 42 is configured to determine an altered and/or adjusted PEEP level in real-time and/or near real-time (e.g., such that a plot like the plot illustrated in FIG. 5 may be generated and/or updated for individual breaths of subject 12). In some embodiments, pressure setting component 42 is configured to determine an amount to alter or adjust PEEP level responsive to manually input instructions received from a user (e.g., via user entry and/or selection of such instructions via user interface 22 and/or other components of system 10). Such alteration may be based on a percentage or specified amount of pressure, e.g., 0.5 to 2 cmH20.

Control component 44 is configured to control pressure generator 14 to generate the pressurized flow of breathable gas. The pressurized flow of gas generated by pressure generator 14 is controlled to replace and/or compliment the regular breathing of subject 12. In some embodiments, control component 44 is configured to cause or instruct pressure generator 14 to generate the pressurized flow of breathable gas in accordance with a prescribed mechanical ventilation therapy regime. In such embodiments, control component 44 is configured to cause pressure generator 14 to control and implement the PEEP level of the positive pressurized flow of breathable gas (e.g., as described above) including introducing an altered or perturbed PEEP level of gas during exhalation of at least one breath (e.g., such as determined by pressure setting component 42). In some embodiments, control component 44 may be configured to control pressure generator 14 to generate the flow of gas in accordance with a ventilation and/or positive airway pressure support therapy regime in addition to and/or instead of a mechanical ventilation therapy regime. By way of non-limiting example, control component 44 may control pressure generator 14 such that the pressure support provided to subject 12 via the flow of gas comprises continuous positive airway pressure support (variable CPAP), variable bi-level positive airway pressure support (Bi-Level PAP), proportional positive airway pressure support (PPAP), and/or other types of pressure support therapy.

In some embodiments, control component 44 is configured to cause pressure generator 14 to adjust the positive pressurized flow of breathable gas temporarily, e.g., during the exhalation of a selected breath, and/or after EFL detection to provide therapy at a set pressure/PEEP level, altered pressure/PEEP level, and/or adjusted pressure/PEEP level as described herein (e.g., including the reset PEEP levels described above or adjusted PEEP level described with reference to FIG. 5), and/or maintain a pressure/PEEP level. Control component 44 is configured to control pressure generator 14 based on information related to the output signals from sensors 18, information determined by classification component 46, pressure setting component 42, and/or parameter component 40, information entered and/or selected by a user via user interface 22, and/or other information.

Generally, processor 20 is configured to receive output signals from sensors 18 and process data read out from the output signals so that reliable information is forwarded to classification component 46. Data collected from sensors 18 may sometimes comprise one or more types of noise signals from the surrounding environment and/or from other sources that affect the accuracy of information read out from the output signals. Processor 20 may be configured to filter out the interfering noise signals based on one or more algorithms such that data after filtering provides more accurate readings related to the real-time measurements of the one or more parameters.

Classification component 46 is a determination module configured to determine whether the exhalation flow response from subject 12 due to the perturbation in PEEP is characterized by EFL or not (e.g., providing a binary (yes-no) classification). Classification component 46 may be configured to analyze waveform characteristics (as measured by one or more sensors 18) of the flow of gas in subject interface 16. It implements an algorithm to automatically determine EFL based on the sensed data such that processor 20 may further automatically set or adjust PEEP level of the pressure generator 14 without waiting for user intervention if the subject has EFL. The classification component 46 receives as an input the data corresponding to exhalation waveform of the breath with perturbed PEEP (perturbed breath) and at least one breath preceding the perturbation (i.e., a reference breath), such as shown by breaths B and A2 (respectively) in FIG. 2. This data is compared and analyzed by classification component 46 to determine EFL. In some embodiments, data corresponding to two or more breaths preceding the perturbation are used as reference data, e.g., breaths A1+A2 of FIG. 2. Utilizing data from two or more breaths will increase the robustness of the algorithm (e.g. by computing an average reference breath) and/or provide assessment of whether the reference breath is sufficiently stable and repeatable so that its comparison with the perturbed breath is not affected by confounding factors.

In accordance with an embodiment, the driving pressure (PEEP) is the only factor altered during ventilation treatment, so changes to the flow waveform as detected at the set PEEP level and perturbed/altered PEEP level are limited for analyzation.

Figure 3:
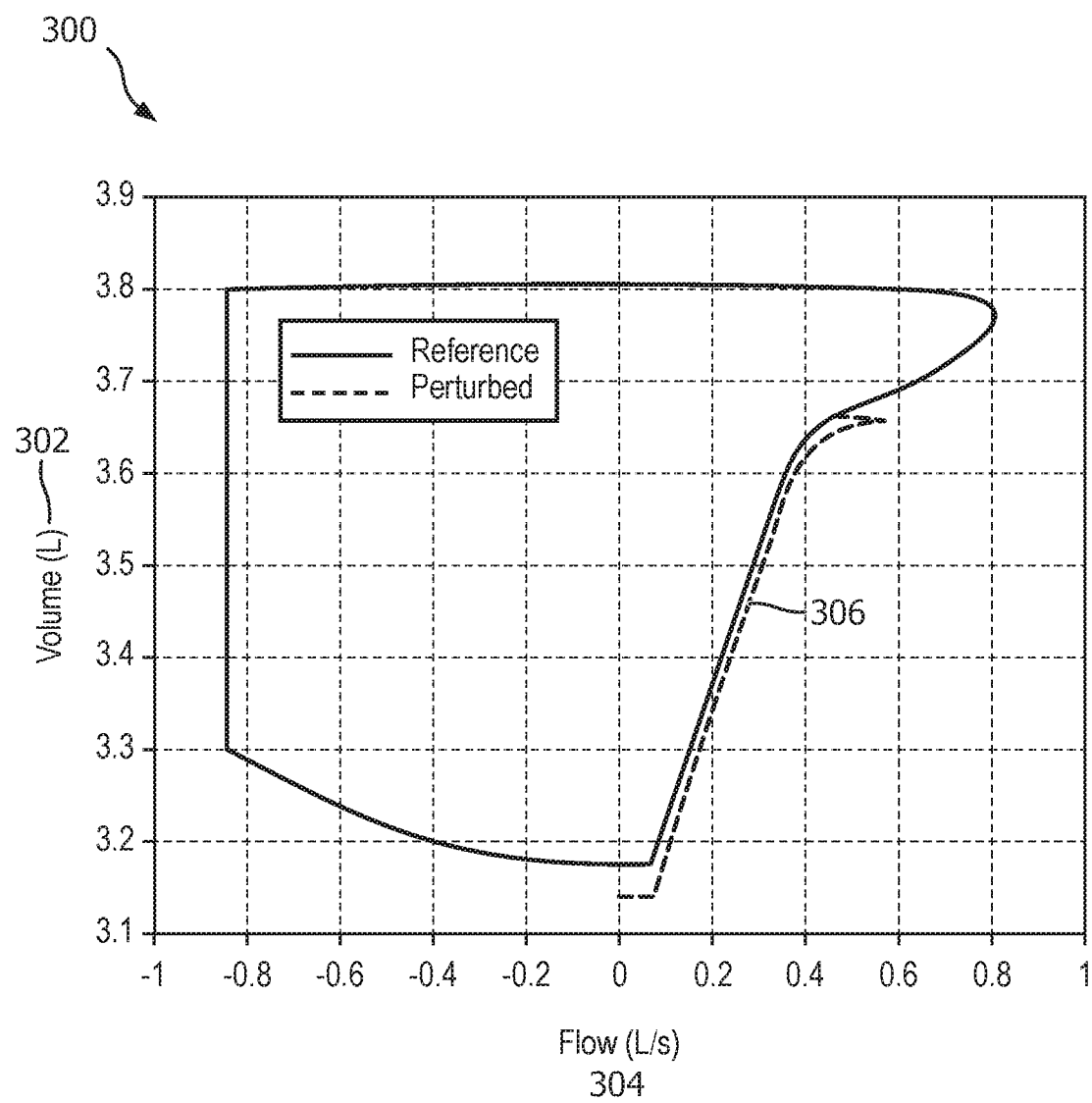
FIG. 3 shows a graphical illustration of flow-volume loops for a reference breath and a perturbed/selected breath for a subject in accordance with an embodiment of this disclosure.
Figure 4:
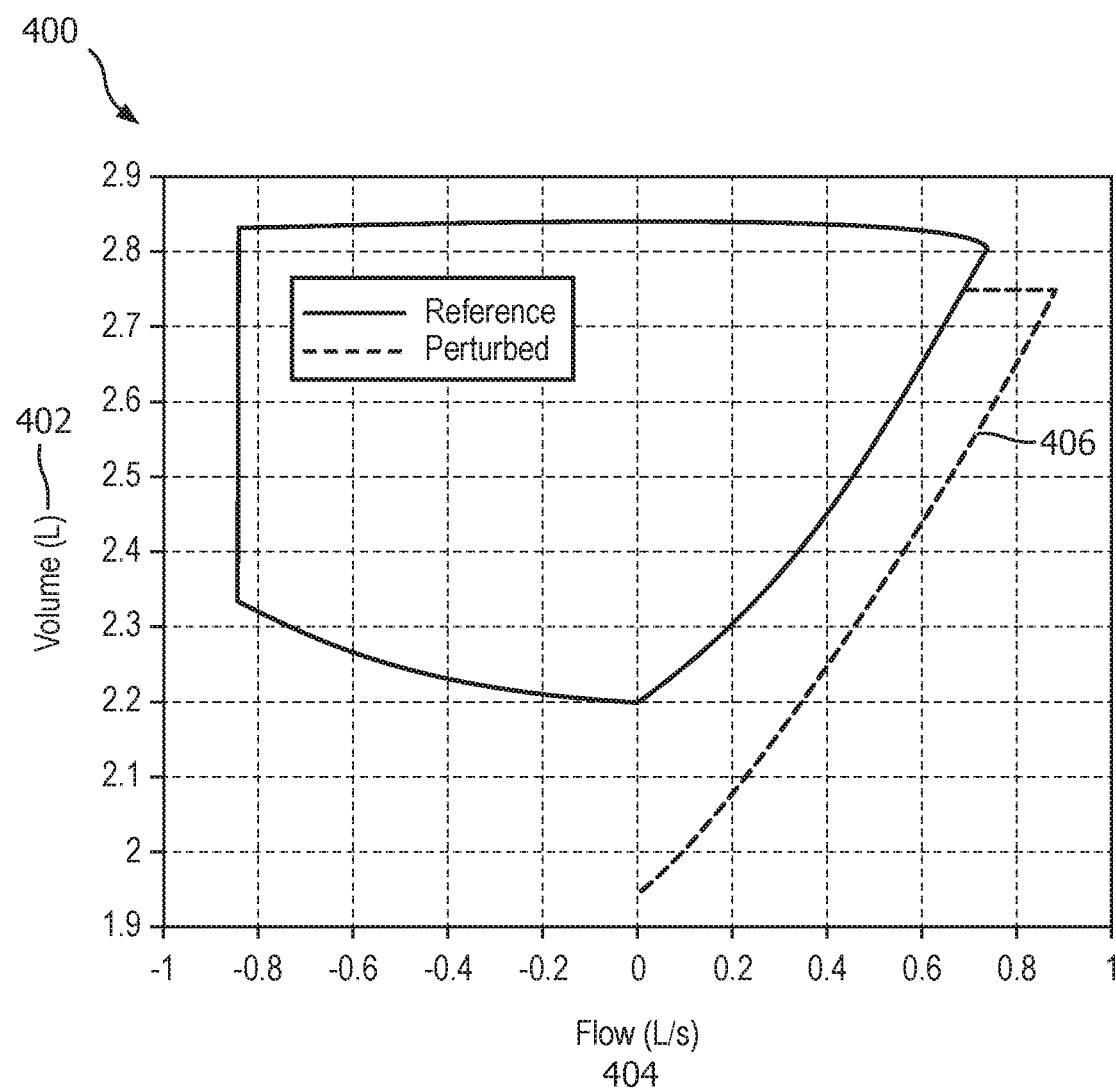
FIG. 4 shows another graphical illustration of flow-volume loops for another reference breath and another perturbed/selected breath for a subject in accordance with an embodiment of this disclosure.

In an embodiment, classification component 46 utilizes mathematical model based detection of EFL by analyzing flow-volume curves built at different levels of PEEP. FIGS. 3 and 4 show flow-volume loops for a reference breath(s) and a perturbed/selected breath, for two different subjects, that may be analyzed by classification component 46 to determine EFL presence, in accordance with embodiments of this disclosure. Classification component 46 is configured to analyze characteristics of both the reference breath(s) and the selected breath and compare the results in order to determine a variation in exhaled flow from subject 12. The variation may occur because the subject's lungs are restricted, inflamed, or deteriorating. In accordance with embodiments, the variation may be compared against a threshold(s). If the variation of the compared flow data exceeds one or more thresholds, then classification component 46 may classify the subject 12 as having limited expiratory flow, and thus determine EFL in the subject 12. If the variation is below or at the threshold, the classification component may classify the subject 12 as having non-limited flow and thus having an absence of EFL.

In other embodiments, the data itself from both the reference breath(s) and the selected breath (with PEEP perturbation) may be compared against a threshold to determine EFL presence.

Referring back to FIGS. 3 and 4, the volume (measured here in liters L) and flow (measured in liters per second, L/s) is charted for both reference breath(s) and a perturbed breath of a subject. In the plot of FIG. 3, the perturbation of PEEP during exhalation does not cause an increase in flow, as shown by both the reference curves being adjacent or close to each other. Accordingly, since there is no increase in flow during the selected exhalation of the breath with altered PEEP, the breath of the subject 12 is considered flow-limited, i.e., the subject has EFL. In the plot of FIG. 4, however, the PEEP perturbation of the selected breath causes a higher exhalation flow, as shown by the variation and spacing of the curves (the variation may further exceed a threshold). Accordingly, the breath of the subject is not flow-limited, i.e., the subject does not have EFL.

One embodiment of the classification algorithm or determination implemented by classification component 46 comprises a single feature computed from the exhalation flow waveform, e.g., the percentage of exhaled volume of air that occurs with the flow from the perturbed breath that is equal to the flow from the reference breath. The exhalation volume waveform may be computed by numerical integration of the measured flow waveform. Among the algorithm parameters to optimize are the threshold, e.g., to determine whether the flows can be considered equal and the threshold in the percentage of exhaled volume to declare a breath flow-limited or not. Another embodiment comprises relating the percentage of exhaled volume to the automatic change in PEEP required to abolish EFL.

Still yet another embodiment of the classification algorithm implemented by classification component 46 is based on multiple features computed from the exhalation flow waveform, including, for example, the percentage of exhaled volume with same flow (reference vs. perturbed breath), the exhaled volume (over the same time for the reference and perturbed breaths), the amplitude of the peak that typically occurs in the perturbed breath.

However, the features or data used to determine the EFL classification is not intended to be limited.

In accordance with an embodiment, the classification algorithm is data-driven and as such it is trained on datasets that include both flow-limited and non-flow-limited breaths (machine learning), and then validated on an independent dataset (excluded from the training phase).

For invasive ventilators, the algorithm to detect EFL may use as an input the flow measured at the outlet of the ventilator or at the patient mouth using one or more sensors 18, such as shown in FIG. 1, at multiple parts of the sensor interface 16. For non-invasive ventilators, the input may be an estimated patient flow that is based on the sensor(s) associated with such as system. In both cases, the volume waveform may be obtained by digital integration of the flow.

FIG. 5 illustrates an exemplary waveform 500 of pressure 502 vs. time 504 for a subject 12 for determining EFL and adjusting PEEP levels, if necessary, based on an output determination for different series of breaths. For example, FIG. 5 illustrates the resulting waveform 500 when a possible set of operations performed by pressure setting component 42 and controller component 44 (FIG. 1) to set and alter PEEP levels, and classification component 46 to determine EFL, are implemented by system 10. As described above, controller component 44 and/or pressure setting component 42 may cause pressure generator 14 (FIG. 1) to generate the pressurized flow of breathable gas at both the set and altered PEEP levels (e.g., 222, 224 in FIG. 2) in subject 12, over a series of breaths (e.g., breaths A1-A2) and at least a single breath (and breath B), respectively, by subject 12. The input to the algorithm of the classification component 46 includes both the perturbed breath and the reference breath (one or multiple breaths preceding the perturbed breath). The reference breath(s) is a first set PEEP level (e.g., 12 cmH20) and the perturbed breath is shown in FIG. 5 as being at a reduced PEEP level (e.g., 5 cmH20). One breath after the perturbed breath is taken at the first set PEEP level (e.g., 12 cmH20). Following the detection of EFL, i.e., 'yes EFL' in FIG. 5, the PEEP level is increased (e.g., to 15 cmH20). A series of breaths are then taken at the increased PEEP level, and the procedure or cycle (e.g., PEEP perturbation, classification algorithm, and PEEP update) repeated after the series of breaths.

If no EFL is detected, i.e., 'no EFL,' in one embodiment, the PEEP level may continue to be provided at the set PEEP level. In another embodiment, the PEEP level may be decreased.

In different embodiments, once the EFL is abolished, i.e., EFL is not detected for one or more cycles, the procedure is repeated at regular time intervals to confirm the absence of EFL or when changes in the breathing pattern are detected.

In the illustrated embodiments of FIGS. 3-5, the PEEP perturbation is shown to be a temporary decrease of PEEP. However, it should be noted that in some embodiments, the PEEP level may be perturbed in the form of an increase of PEEP level.

Returning to FIG. 1, in some embodiments, pressure setting component 42 is configured to determine an altered and/or adjusted pressure/PEEP level in real-time and/or near real-time (e.g., such that a plot like the plot illustrated in FIG. 5 may be generated and/or updated for individual breaths of subject 12). In some embodiments, pressure setting component 42 is configured to determine an amount to alter or adjust pressure/PEEP level responsive to manually input instructions received from a user (e.g., via user entry and/or selection of such instructions via user interface 22 and/or other components of system 10), and control component 44 implements such features in the pressure generator. Such alteration may be based on a percentage or specified amount of pressure, e.g., approximately 0.5-2.0 cmH2O (inclusive).

User interface 22 is configured to provide an interface between system 10 and subject 12 and/or other users through which subject 12 and/or other users provide information to and receive information from system 10. Other users may comprise a caregiver, a doctor, a clinician, a family member, a decision maker, and/or other users. User interface 22 enables data, cues, results, and/or instructions and any other communicable items, collectively referred to as "information," to be communicated between a user (e.g., subject 12) and one or more of pressure generator 14, sensors 18, processor 20, electronic storage 24, and/or other components of system 10. For example, user 36 may input one or more parameters related to the flow of gas initially delivered to subject 12, including but not limited to the pressure level (PEEP level) and duration of a pulse, which are further transmitted to processor 20 to control pressure generator 14 to generate the flow of gas in accordance with the inputted one or more parameters. In some embodiments, information entered through user interface 22 to system 10 may include ventilation therapy initial percussive pressure waveform parameters, frequency range, an oscillating flow rate amplitude effectiveness threshold, and/or other information.

Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 22 comprises a plurality of separate interfaces. In some embodiments, user interface 22 comprises at least one interface that is provided integrally with pressure generator 14. In some embodiments, user 36 of the interface 22 may include subject 12, a clinician, a nurse, any caregiver, an interested party, and/or any other entities.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

Optionally, system 10 may include a network 56 for communication with one or more of the processor 20, user interface 22, and/or electronic storage 24. Network 56 is configured to transmit information among a plurality of network components. For example, network 56 receives inputs from user 36 at user interface 22 related to one or more parameters associated with the therapeutic flow of gas for the purpose of therapy and transmits these inputs to processor 20 for further processing. In some embodiments, a request inputted via user interface 22 is received at server 38 via network 56 to retrieve historical information related to past therapies on the subject and/or other subjects for analysis. Network 56 forwards an instruction from server 38 to retrieve the requested historical information related to past therapies on a plurality of subjects from electronic storage 24. Network 56 may be a single network or a combination of multiple networks. For example, network 56 may be a local area network (LAN), a wide area network (WAN), a public network, a private network, a proprietary network, a Public Telephone Switched Network (PSTN), the Internet, a wireless communication network, a virtual network, and/or any combination thereof.

Electronic storage 24 is configured to electronically store information in an electronic storage media. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 24 may store software algorithms or packages, information related to past therapies, information related to a plurality of subjects that receive various therapies, information determined and/or processed by processor 20, information received via user interface 22, and/or other information that enables system 10 to function as described herein. Electronic storage 24 may be (in whole or in part) a separate component within system 10, or electronic storage 24 may be provided (in whole or in part) integrally with one or more other components of system 10 (e.g., user interface 22, processor 20, etc.).

Figure 6:
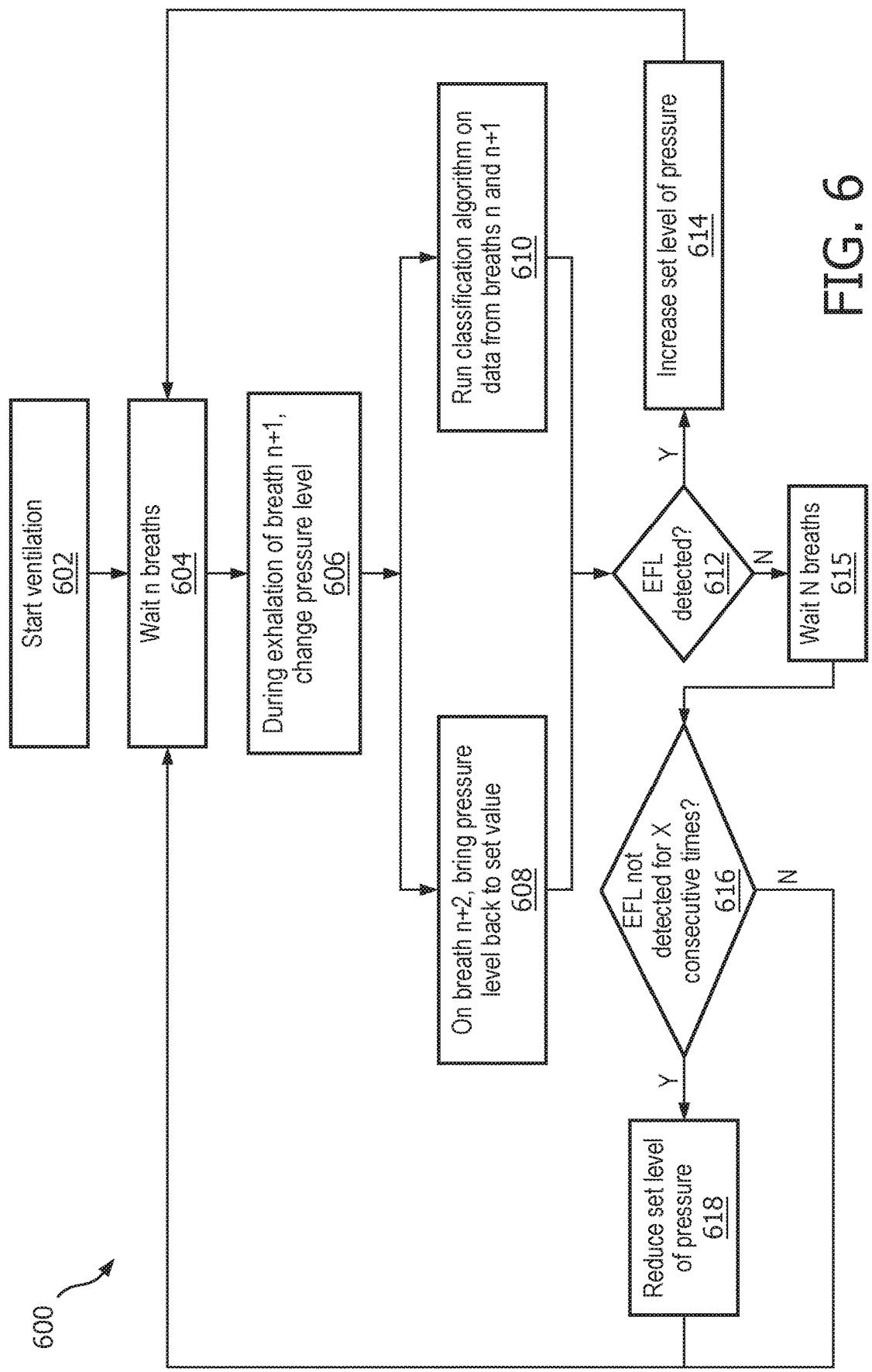
FIG. 6 is a flow chart or algorithm for a method of detecting EFL by controlling positive pressure applied during expiration of a breath in the subject in accordance with an embodiment of this disclosure.

FIG. 6 illustrates a method 600 for determining EFL by controlling positive pressure applied to a subject, e.g., with a mechanical ventilator system. The system comprises a pressure generator, one or more sensors, one or more hardware processors, and/or other components, such as those illustrated in system 10 of FIG. 1. The one or more hardware processors 20 are configured by machine-readable instructions to execute computer program components. The computer program components include a parameter component 40, a pressure setting component 42, a control component 44, classification component 46, and/or other components. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, ventilation is started such that a positive pressurized flow of breathable gas at a set pressure level (e.g., a set PEEP level) is generated by the pressure generator and delivered to the airway of a subject. In some embodiments, operation 602 is performed by a pressure generator the same as or similar to pressure generator 14 (shown in FIG. 1 and examples described herein). In some embodiments, the pressure/PEEP level is set by a processor component(s) the same as or similar to parameter component 40 (shown in FIG. 1 and described herein), pressure setting component 42, control component 44, and/or even another user, e.g., user 36.

At an operation 604, the positive pressurized flow of gas is delivered from the pressure generator at the set pressure level for n breaths, or a series of breaths, to the subject. n may equal more than one breath, e.g., two or more breaths, in accordance with an embodiment, that are taken in series at the set pressure/PEEP level. However, it is not to say that method 600 cannot be implemented, in accordance with another embodiment, wherein n may equal a single breath at the set pressure level at operation 604. Output signals, e.g., from one or more sensors like sensors 18, conveying information related to breathing of the subject for the n breaths or series of breaths are generated at operation 604 and forwarded for processing, e.g., to processor 20. In some embodiments, the one or more sensors comprise a flow rate sensor configured to generate output signals conveying information related to a flow rate of the pressurized flow of breathable gas, a pressure sensor conveying information related a pressure of breathable gas at a mouth of the subject, a volume sensor conveying information corresponding to flow volume, lung volume, output volume, etc., and/or other sensors.

At an operation 606, the pressure level of the positive pressurized flow of breathable air from the pressure generator being delivered to the subject is altered or changed during exhalation of breath n+1. In some embodiments, operation 606 of changing the pressure level (e.g., changing or altering the PEEP level) for breath n+1 is caused or implemented by a processor component(s) the same as or similar to control component 44, pressure setting component 42, and/or parameter component 40 (shown in FIG. 1 and described herein). The amount of change or perturbation may be determined any number of ways, such as those described previously. Output signals, e.g., from one or more sensors like sensors 18, conveying information related to breathing of the subject for at least the one selected breath n+1 are generated and forwarded for processing, e.g., to processor 20. In some embodiments, the one or more sensors comprise a flow rate sensor configured to generate output signals conveying information related to a flow rate of the pressurized flow of breathable gas, a pressure sensor conveying information related to a pressure of breathable gas at a mouth of the subject, a volume sensor conveying information corresponding to flow volume, lung volume, output volume, etc., and/or other sensors.

At an operation 608, the pressure level is reset to the set pressure level (e.g., set PEEP level) for a subsequent breath n+2, for delivery to the subject by the pressure generator. In some embodiments, the setting of pressure generator back to the set pressure level and delivering of pressurized flow at operation 608 is caused or implemented by a processor component the same as or similar to control component 44, pressure setting component 42, and/or parameter component 40 (shown in FIG. 1 and described herein).

Additionally, the determination of EFL in the subject is implemented by utilizing the output signals from both operations 604 and 606, i.e., data or information relating to exhalation for the n breaths (or series of breaths) at the set pressure level and exhalation for the at least one breath n+1 is used and analyzed at operation 610 to determine EFL. For example, a binary classification algorithm may be used to confirm either a presence of EFL or an absence of EFL using the collected data from breaths n and breath n+1. In some embodiments, a comparison of data, such as the volume and flow data illustratively shown in FIGS. 3 and 4, or percentage of exhaled volume of air, may be used for processing and determining EFL. The processing at operation 610 may be performed, in some embodiments, by classification component 46 (shown in FIG. 1 and described herein).

At operation 612, a determination is made to see if EFL is detected. The determination at operation 612 may be performed, in some embodiments, by classification component 46 (shown in FIG. 1 and described herein).

If EFL is detected, i.e., YES in response to operation 612, at operation 614, a set level of pressure of the pressure generator is automatically adjusted, e.g., increased, for delivery to the subject at the adjusted pressure level. In some embodiments, operation 614 of increasing the pressure level is caused or implemented by a processor component(s) the same as or similar to control component 44, pressure setting component 42, and/or parameter component 40 (shown in FIG. 1 and described herein). Thereafter, the delivery cycle restarts at operation 604, wherein the pressure generator is configured to deliver a pressurized flow of breathable gas to a subject for n breaths at the adjusted/increased pressure level.

Alternatively, if EFL is not detected at 612, i.e., NO, then an operation 615 may be optionally implemented to wait a number N breaths wherein the pressurized flow of gas is delivered from the pressure generator at the set PEEP level for N breaths, or a series of breaths, to the subject. In one embodiment, if EFL is not detected on the last perturbation, the system/method includes waiting N+n breaths before performing a new cycle and perturbation or alteration in pressure (at shown at operations 604 and 606).

Operation 616 may be optionally implemented to determine if EFL has not been detected for X consecutive times, or cycles. In one embodiment, the X consecutive times corresponds to a number of breaths, e.g., one hundred (100) breaths. In accordance with another embodiment, the operation at 616 references a number of X consecutive times of cycles, wherein a cycle is defined in method 600 to include operations 604-612. That is, it may be determined if, after a number X (i.e., more than 1) of cycles (including waiting and breathing n breaths at the set pressure level and altering pressure level for at least one breath n+1 have been introduced to the subject), result in EFL not being detected (i.e., a detection that EFL is absent in the subject for X consecutive times). In some embodiments, operation 616 is implemented by a processor component(s) the same as or similar to classification component 46. If the number of consecutive times (or cycles) has not yet equaled X (or surpassed X) for determining that EFL is absent in a subject, i.e., NO in response to operation 616, the cycle is repeated by starting a delivery of pressurized flow of breathable gas for n breaths by the pressure generator at the set pressure level at operation 604. On the other hand, if EFL is not detected for X consecutive times, i.e., YES in response to operation 616, then the pressure generator is caused to automatically adjust, e.g., decrease or reduce, the set pressure level of the pressurized flow of breathable gas at operation 618. In some embodiments, the adjusting/decreasing may optionally be implemented after n breaths. In some embodiments, operation 618 of decreasing the pressure level of the pressure generator is caused or implemented by a processor component(s) the same as or similar to control component 44, pressure setting component 42, and/or parameter component 40 (shown in FIG. 1 and described herein). After the pressure level adjustment, the cycle restarts at operation 604, wherein the pressure generator is configured to deliver a pressurized flow of breathable gas to a subject for n breaths at the adjusted (e.g., decreased) pressure level, and continue the cycle/method 600 as needed (e.g., until EFL is abolished or the subject stops treatment).

In accordance with an embodiment, either of operations 615 or 616 need not be implemented. After EFL is not detected at operation 612, for example, the method 600 may automatically adjust/decrease the level of pressure for delivery by the pressure generator to the subject, as shown at operation 618.

The adjusted pressure level may be determined based on the exhaled volume of air and/or other information as previously described.

In an embodiment, the pressure level is incrementally changed until EFL is abolished in the subject.

Also, in accordance with some embodiments, a perturbation to a selected or single breath may be implemented in the disclosed method 600 and by the disclosed system 10 based on analyzing data (e.g., that is sensed or determined by sensor(s) 18, for example), in addition or alternatively to causing the pressure generator to temporarily alter the pressure level as previously described in the operations above (e.g., after waiting n breaths at operation 604). For instance, the detection or presence of intrinsic PEEP (PEEPi) (i.e., a positive end-expiratory pressure caused by an incomplete exhalation) may be used in accordance with embodiments to command a new perturbation to the subject, since PEEPi is typically associated with EFL.

Although the above method 600 and this disclosure has described and shown in the Figures a particular number of breaths and times corresponding to the same, it should be noted that the number of breaths and amount of time (e.g., for inhalation and/or exhalation) is not intended to be limited. Any number of breaths may be taken at a set or altered or adjusted pressure level, for any period (seconds) of time.

The system and method disclosed herein may be implemented in new or incorporated into existing ventilator hardware (as opposed to traditional forced oscillation techniques (FOT) and negative expiratory pressure (NEP) methods) because it does not require modification of known systems. It can be applied to different ventilator support devices (CPAP, BiPAP, NIV), and at best, only the training of the classification algorithm and EFL detection would possibly need to be re-tuned for different devices. For example, in the case of a CPAP device, after a period of time, a negative pressure or pressure drop may be implemented during expiration of a selected breath. With a valve-based system, e.g., PEP valve, the adjustment device may be adjusted to increase/decrease the amount of expiratory pressure the subject must expel. It should be understood that additional devices may be used with such systems, e.g., flow sensors, electronics, etc. to allow for readings and control of the adjustment of positive pressure during expiration.

Generally, the disclosed method and algorithm is based on a similar principle of the current practice of manual abdomen compression, but it is completely automated, overcoming variability and subjectivity of manual procedures. A temporary perturbation of positive pressure during exhalation on selected breaths provides readings and data that may be used to detect EFL, since responses to such a perturbation are different if the subject has flow-limited breaths as compared to non-flow limited breaths. Accordingly, upon detection of EFL in a subject, the ventilator/system may be programmed to automatically adjust the level of pressure, in order to eliminate or abolish EFL.

Although this disclosure is described with reference to detecting and treating EFL, system 10 and method 600 may be used to treat subjects 12 suffering from COPD, Acute Respiratory Distress Syndrome (ARDS), hypercapnia, and/or other breathing conditions. System 10 and method 600 may be configured to provide pressure support therapy (e.g., Continuous Positive Airway Pressure (CPAP), Biphasic Positive Airway Pressure (BiPAP)) with pressure levels to open airways of a subject.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A system for determining expiratory flow limitation (EFL) by controlling positive pressure applied during expiration of a breath in a subject, the system comprising:
a pressure generator configured to generate a positive pressurized flow of breathable gas for delivery to an airway of the subject;
one or more sensors configured to generate output signals conveying information related to breathing of the subject; and one or more hardware processors operatively coupled to the pressure generator and the one or more sensors and configured by machine-readable instructions to:
cause the pressure generator to deliver the positive pressurized flow of breathable gas at a set pressure level to the subject for a series of breaths;
for at least one selected breath in the series of breaths, cause the pressure generator to temporarily alter the pressure level of the positive pressurized flow of breathable gas to a pressure that is different from the set pressure level for delivery to the subject during exhalation of the at least one selected breath;
determine EFL in the subject using the output signals from the one or more sensors conveying information related to (a) exhalation for the series of breaths of the subject at the set pressure level and (b) exhalation for the at least one selected breath at the altered pressure level; and
automatically adjust, without user intervention, the set pressure level of the pressure generator based on the EFL determination for delivery of the positive pressurized flow of breathable gas to the subject at an adjusted pressure level for at least one subsequent breath.

2. The system of claim 1, wherein the one or more hardware processors are configured to: cause the pressure generator to return to the set pressure level and deliver the positive pressurized flow of breathable gas at the set pressure level after exhalation of the at least one selected breath for the at least one subsequent breath and before automatically adjusting the set pressure level of the pressure generator.

3. The system of claim 1, wherein the delivery of positive pressurized flow of breathable gas at the set pressure level comprises the one or more hardware processors being configured to cause the pressure generator to deliver the breathable gas at the set pressure level for N number of breaths, wherein the temporary delivery of the positive pressurized flow of breathable gas to the subject during exhalation at an altered pressure level comprises the one or more hardware processors being configured to cause the pressure generator to deliver the breathable gas at the altered pressure level for breath N+1; and wherein the one or more hardware processors are further configured to reset the positive pressurized flow of breathable gas of the pressure generator at the set pressure level for breath N+2 and cause the pressure generator to deliver the pressurized flow of breathable gas at the set pressure level to the subject.

4. The system of claim 1, wherein the one or more hardware processors are configured such that the temporary delivery of the positive pressurized flow of breathable gas at the altered pressure level during exhalation of the at least one selected breath comprises:
the one or more hardware processors being configured to cause the pressure generator to adjust the positive pressurized flow of breathable gas by decreasing the pressure level from the set pressure level such that, during exhalation, the positive pressurized flow of breathable gas delivered the subject is reduced in pressure for the at least one selected breath.

5. The system of claim 1, wherein the one or more hardware processors are configured such that determining EFL in the subject comprises:
receiving first exhalation flow data corresponding to at least one reference breath in the series of breaths,
receiving second exhalation flow data corresponding to the at least one selected breath;
comparing the first and second exhalation flow data; and
determining, based on the compared flow data exceeding one or more thresholds, whether exhalation of the at least one selected breath is characterized by EFL,
wherein the first exhalation flow data for at least one reference breath is obtained by the one or more sensors before the second exhalation flow data of the selected breath.

6. The system of claim 5, wherein the one or more hardware processors are configured to:
confirm EFL in the subject using the determination;
cause the pressure generator to adjust the positive pressurized flow of breathable gas by increasing the pressure level from the set pressure level for delivery to the subject for a series of subsequent breaths;
for a second selected breath after the series of subsequent breaths, cause the pressure generator to temporarily change the pressure level of the positive pressurized flow of breathable gas for delivery to the subject during exhalation of the second selected breath; and
determine EFL in the subject using the output signals from the one or more sensors conveying information related to (a) exhalation for the at least one breath of the subject at the set pressure level and (b) exhalation for the at least one selected breath at the changed pressure level.

7. The system of claim 5, wherein the one or more hardware processors are configured to:
confirm absence of EFL in the subject using the determination;
cause the pressure generator to adjust the positive pressurized flow of breathable gas by decreasing the pressure level from the set pressure level for delivery to the subject for a series of subsequent breaths.

8. A method for determining expiratory flow limitation (EFL) by controlling positive pressure applied during expiration of a breath in a subject with a system, the system comprising a pressure generator, one or more sensors, and one or more hardware processors, the method comprising:
generating, with the pressure generator, a positive pressurized flow of breathable gas at a set pressure level and at an altered pressure level that has a different positive pressure from that of the set pressure level for delivery to an airway of the subject;
generating, with the one or more sensors, output signals conveying sensed information related to (a) exhalation for a series of breaths of the subject at the set pressure level and (b) exhalation for at least one selected breath at the altered pressure level;
determining, using the one or more hardware processors, a percentage of exhaled volume of air for (a) at least one reference breath from the series of breaths and (b) the at least one selected breath based on the generated output signals of the sensed information;
comparing, using the one or more hardware processors, the determined percentage of exhaled volume of air for both the at least one reference breath and the at least one selected breath;
determining, using the one or more hardware processors, EFL in the subject based on the comparison; and
causing, using the one or more hardware processors, automatic adjustment, without user intervention, of the set pressure level of the pressure generator based on the EFL determination for delivery of the positive pressurized flow of breathable gas to the subject at an adjusted pressure level for at least one subsequent breath.

9. The method of claim 8, wherein the method further comprises using the one or more hardware processors to cause the pressure generator to return to the set pressure level and deliver the positive pressurized flow of breathable gas at the set pressure level after exhalation of the at least one selected breath for the at least one subsequent breath and before the causing of the automatic adjustment of the set pressure level of the pressure generator.

10. The method of claim 8, wherein the generation of the positive pressurized flow of breathable gas at the set pressure level and at the altered pressure level comprises: causing, using the one or more hardware processors, the pressure generator to deliver the positive pressurized flow of the breathable gas to the subject at the set pressure level for N number of breaths and to deliver the positive pressurized flow of breathable gas to the subject at the altered pressure level for breath N+1; and wherein the method further comprises using the one or more hardware processors to reset the positive pressurized flow of breathable gas of the pressure generator at the set pressure level for breath N+2 to cause the pressure generator to deliver the positive pressurized flow of breathable gas at the set pressure level to the subject.

11. The method of claim 8, wherein the generation of the positive pressurized flow of breathable gas at the altered pressure level comprises causing, using the one or more hardware processors, the pressure generator to adjust the positive pressurized flow of breathable gas by decreasing the pressure level from the set pressure level such that, during exhalation, the positive pressurized flow of breathable gas delivered the subject is reduced in pressure for the at least one selected breath.

12. The method of claim 8, wherein the determining EFL comprises confirming EFL in the subject, and wherein the causing the automatic adjustment comprises:
   causing the pressure generator to adjust the positive pressurized flow of breathable gas by increasing the pressure level from the set pressure level for delivery to the subject for a series of subsequent breaths;
   for a second selected breath after the series of subsequent breaths, causing the pressure generator to temporarily change the pressure level of the positive pressurized flow of breathable gas for delivery to the subject during exhalation of the second selected breath; and
   determining, using the one or more hardware processors, EFL in the subject using the output signals from the one or more sensors conveying sensed information related to (a) exhalation for the at least one breath of the subject at the set pressure level and (b) exhalation for the at least one selected breath at the changed pressure level.

13. The method of claim 8, wherein the determining EFL comprises confirming the absence of EFL in the subject, and wherein the causing the automatic adjustment comprises causing the pressure generator to adjust the positive pressurized flow of breathable gas by decreasing the pressure level from the set pressure level for delivery to the subject for a series of subsequent breaths.

14. The method of claim 8, wherein the determining EFL comprises determining whether the compared flow data exceeds one or more thresholds, and wherein the sensed information for at least one reference breath from the series of breaths is obtained by the one or more sensors before the sensed information of the selected breath.

15. The method of claim 8, wherein the comparing further comprises: comparing a measured exhaled volume for both the at least one reference breath and the at least one selected breath and/or comparing an amplitude of pressure for both the at least one reference breath and the at least one selected breath.

16. A system for determining expiratory flow limitation (EFL) by controlling positive pressure applied during expiration of a breath in a subject, the system comprising:
   means for generating a positive pressurized flow of breathable gas at a set pressure level and at an altered pressure level that has a different pressure from that of the set pressure level for delivery to an airway of the subject;
   means for generating output signals conveying sensed information related to (a) exhalation for a series of breaths of the subject at the set pressure level and (b) exhalation for at least one selected breath at the altered pressure level;
   means for determining EFL in the subject by comparing data from the output signals of at least one reference breath from the series of breaths and the at least one selected breath against a threshold; and
   means for automatically adjusting, without user intervention, the set pressure level of the means based on the EFL determination for delivery of the positive pressurized flow of breathable gas to the subject at an adjusted pressure level for at least one subsequent breath.

17. The system of claim 16, further comprising:
   means for determining a percentage of exhaled volume of air for both the at least one reference breath and the at least one selected breath based on the generated output signals of the sensed information; and
   means for comparing at least the determined percentage of exhaled volume of air for both the at least one reference breath and the at least one selected breath, wherein the means for determining EFL utilizes the comparison.

18. The system of claim 16, wherein the means for generating the positive pressurized flow of breathable gas are configured to return to the set pressure level and deliver the positive pressurized flow of breathable gas at the set pressure level after exhalation of the at least one selected breath for at least one subsequent breath and before the automatic adjusting of the set pressure level of the pressure generator.

19. The system of claim 16, wherein the means for generating the positive pressurized flow is configured to deliver the positive pressurized flow breathable gas at the set pressure level for N number of breaths and to deliver the positive pressurized flow of breathable gas to the subject at the altered pressure level for breath N+1; and wherein means for generating the pressurized flow is further configured to:
   reset the positive pressurized flow of breathable gas of the pressure generator at the set pressure level for breath N+2 and cause the pressure generator to deliver the positive pressurized flow of breathable gas at the set pressure level to the subject.

20. The system of claim 16, wherein the means for determining EFL is configured to:
   confirm EFL in the subject;
   cause the means to adjust the positive pressurized flow of breathable gas by increasing the pressure level from the set pressure level for delivery to the subject for a series of subsequent breaths;
   for a second selected breath after the series of subsequent breaths, cause the means to temporarily change the pressure level of the positive pressurized flow of breathable gas for delivery to the subject during exhalation of the second selected breath; and determine EFL in the subject using the output signals from the one or more sensors conveying information related to (a) exhalation for the at least one breath of the subject at the set pressure level and (b) exhalation for the at least one selected breath at the changed pressure level.

21. The system of claim 16, wherein the means for determining EFL is configured to:
   confirm absence of EFL in the subject; and
   cause the means for generating the positive pressurized flow to decrease the pressure level from the set pressure level for delivery to the subject for a series of subsequent breaths.

22. The system of claim 16, wherein the means for determining EFL is configured to: determine whether the compared flow data exceeds one or more thresholds, and wherein the sensed information for at least one reference breath from the series of breaths is obtained by the means for generating output signals before the sensed information of the selected breath.

23. The system of claim 16, wherein the comparing by the means for determining EFL further comprises the means being configured to compare a measured exhaled volume for both the at least one reference breath and the at least one selected breath and/or compare an amplitude of pressure for both the at least one reference breath and the at least one selected breath.

* * * * *